United States Patent [19]

Arena et al.

[11] Patent Number: 5,073,654

[45] Date of Patent: Dec. 17, 1991

[54] SYNTHESIS OF THE 5- AND 6-METHYLTETRALINS BY CONTINUOUS METHYLATION OF TETRALIN

[75] Inventors: Blaise J. Arena, Des Plaines; Paul R. Kurek, Barrington, both of Ill.

[73] Assignee: UOP, Des Plaines, Ill.

[21] Appl. No.: 633,873

[22] Filed: Dec. 26, 1990

[51] Int. Cl.$^5$ .............................................. C07C 2/68
[52] U.S. Cl. ................................................... 585/467
[58] Field of Search ........................ 585/463, 467, 468

[56] References Cited

U.S. PATENT DOCUMENTS 3,187,063  6/1965  Burk et al. ........................... 585/468
3,242,221  3/1966  Kovach et al. ..................... 585/468

Primary Examiner—Anthony Mc Farlane
Assistant Examiner—Nhat Phan
Attorney, Agent, or Firm—Thomas K. McBride; Eugene I. Snyder

[57] ABSTRACT

Continuous methylation of tetralin with methanol over several solid acid catalysts affords a mixture of 5-methyltetralin and 6-methyltetralin with selectivity of better than 65% at high conversions. Zeolite $\beta$ is a particularly effective catalyst insofar as it catalyzes the reaction at a temperature approximately 100° C. lower than that required for silica-aluminas. However, the reaction temperature is quite sensitive to the concentration of methanol in the feedstock.

9 Claims, 2 Drawing Sheets

SYNTHESIS OF THE 5- AND 6-METHYLTETRALINS BY CONTINUOUS METHYLATION OF TETRALIN

BACKGROUND OF THE INVENTION

The various monomethylated tetralins are among a host of solvents which may be used as a desorbent in separations, such as those using a simulated moving bed, such as Sorbex TM separations technology (see, for example, Handbook of Petroleum Refining Processes, edited by Robert A. Meyers, 8–80 et ff., McGraw-Hill Book Company (1986)). However, the full exploitation of these methyltetralins is currently limited by their availability. It also has been found that the desorption properties of the 5- and 6-methyltetralins are quite sensitive to components other than the methyltetralins. Therefore it is necessary not only to prepare the requisite materials in commercial quantities, but it is also necessary that their preparation be relatively inexpensive, and that any method used leads, at the very least, to mixtures of the monomethyltetralins containing little polyalkylated material or other components deleterious to the use of the monomethyltetralins as desorbents.

Bouncer, EP 160145A, has taught that tetralin can be selectively monoalkylated with olefins using as catalysts a wide pore amorphous silica-alumina. Muganlinsk et al., SU1076424-A have obtained [presumably] monoalkyltetralins in 95–98% yield by alkylating tetralins with aliphatic alcohols containing 4 to 10 carbon atoms using a sulfated silica-alumina (approximately 7:1) containing iron oxide, calcium oxide, and magnesium oxide. However, it seems likely that alkylation occurs via olefin arising from the alcohol, since olefinic oligomers are the principal side products of the reaction. The patentee in J81009958-B used a 7:1 silica-alumina in the alkylation of tetralin with propylene to give 6-isopropyltetralin in 92% yield. More recently Innes et al., U.S. Pat. No. 4,891,458, have used zeolite $\beta$ to alkylate aromatic hydrocarbons with olefins of 2–4 carbon atoms in the liquid phase, claiming that zeolite $\beta$ has a higher selectivity to the monoalkyl products and a longer catalyst lifetime than other zeolites.

Preparation of the monomethyltetralins can not be effected by olefinic alkylation. Furthermore, methylation using methanol as the alkylating agent is notoriously more difficult than analogous alkylations using higher alcohols. Consequently, the prior art is of limited value in identifying satisfactory processes and catalysts for the preparation of monomethyltetralins. In addition, any process is subject to a number of constraints dictated by the economy of methyltetralin production and by the required product purity. In particular, it is necessary to have the conversion of tetralin in the methylation reaction as high as possible to maximize product formation. Conversions of tetralin (as defined within) of greater than 95% are ideal, although conversions as low as about 65% are acceptable if compensated by other factors. Another limitation is that the selectivity of 5- and 6-methyltetralin production should be at least 65%. Selectivity is defined as the percentage of reaction product which is 5- and 6-methyltetralin. The reaction product consists not only of alkylated tetralins, but also of unidentified decomposition products of tetralin itself. The latter are particularly irksome and deleterious, for they give the reaction product an objectionable color, removable if at all only with great difficulty, which may seriously impair the acceptability of the monomethyltetralins as desorbents, and which also may impair their desorbent properties.

We have found a regime of alkylation conditions which produces methyltetralin with a selectivity of at least 65%, usually at least 75%, at a tetralin conversion of at least 65%, often greater than 80%, and occasionally greater than 90%. Because tetralin decomposition seems to be an unavoidable concomitant of alkylation, and because tetralin decomposition products are deleterious to the contemplated use of the 5- and 6-methyltetralins, the reaction conditions are further circumscribed by the requirement that there be less than 120% conversion of tetralin. The acceptable reaction regime encompasses a relatively narrow range of tetralin to methanol proportions, a relatively narrow selection of solid acidic catalysts, and a limited temperature range which is a complicated, often puzzling function of all of the foregoing.

Although we have found that certain silica-aluminas may be used as catalysts in our process, we have determined that zeolite $\beta$ is a superior catalyst. Its superiority is associated with the fact that it is a significantly more active catalyst than the silica-aluminas while being equally selective. This means that the selective alkylation of tetralin with methanol can be performed with zeolite $\beta$ at a significantly lower temperature than that possible with the silica-aluminas. There are several attendant beneficial consequences to this greater activity. One is that the reaction can be run to high conversion with high selectivity and with very little tetralin decomposition, thereby affording a higher quality product. Secondly, because the product quality is less sensitive to temperature, the overall process is not so sensitive to operator or process control error. Additionally, as the catalyst becomes deactivated there is a greater range over which the temperature may be raised to compensate for catalyst deactivation before reactant decomposition becomes an issue. Because zeolite $\beta$ is more active than the silica-aluminas, less of zeolite $\beta$ is required to catalyze the reaction at a given production rate, thereby enhancing process economics. These advantages are substantial and may be unique to zeolite $\beta$.

SUMMARY OF THE INVENTION

The purpose of this invention is to prepare 5-methyltetralin and 6-methyltetralin by methylating tetralin at high yield, with good selectivity, and with minimum product contamination by decomposition products of tetralin, especially color bodies. An embodiment comprises the reaction of methanol and tetralin over a solid acid catalyst. In a more specific embodiment the solid acid catalyst is zeolite $\beta$. In a yet more specific embodiment the tetralin-methanol reaction mixture is from about 1.4 to about 24 molar proportions of tetralin relative to methanol. In still another embodiment the methylation of tetralin is performed continuously using a fixed catalyst bed.

BRIEF DESCRIPTION OF THE FIGURES

FIG. 1, Catalyst A; FIG. 2, Catalyst B; FIG. 3, Catalyst C; FIGS. 4–7, Zeolite $\beta$ using 1.85%, 2.6% 3.2%, and 6.3% methanol in feed, respectively.

DESCRIPTION OF THE INVENTION

Figure 1:
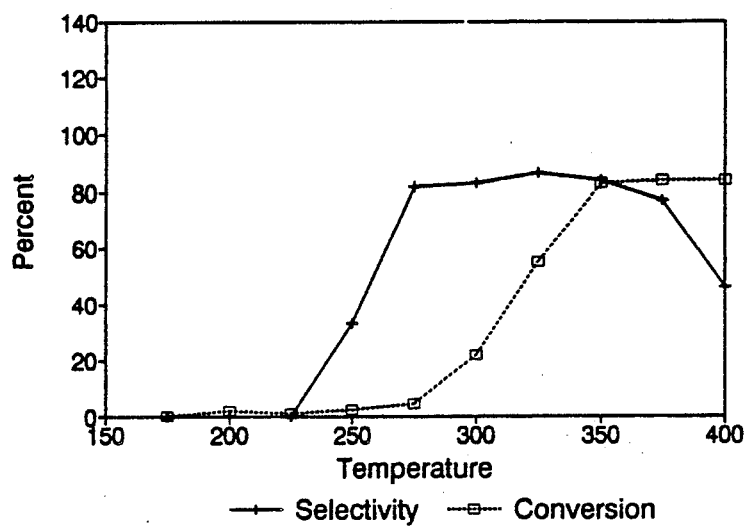
FIGS. 1–7 are graphical representations of the average selectivity and average conversion observed with various catalysts as a function of temperature, and correspond to the data in Table 5. The correspondence between figures and catalysts is as follows.

The preparation of 5- and 6-methyltetralin by methylation of tetralin using acidic catalysts is only a partial solution to the need of obtaining these methyltetralins as a desorbent in separation processes. Of paramount importance is the need for preparing these monomethyltetralins as a relatively pure mixture. In particular, it is critical to have in the mixture a minimum of color bodies, attributable to the decomposition of tetralin itself under methylation conditions. It also is of great importance to methylate tetralin with as high a selectivity as possible to maximize initial product purity, for other reaction products can adversely effect the properties of methyltetralin as a desorbent. Both of the foregoing requirements optimally are met while conducting the reaction at conversions of tetralin of at least 65%, preferably of at least 80%, and more desirably of about 90%, in a continuous reaction over a solid catalyst bed. We have found a group of solid acid catalysts which meet all of the stated criteria. Even with the group of successful catalysts, the effect of varying molar proportions of tetralin relative to methanol has an important bearing on the outcome of methylation, for only a certain regime is experimentally acceptable. And even within this narrow reaction regime not all catalysts are equivalent, for zeolite $\beta$ excels in performance.

The reaction of interest in this application is the methylation of tetralin to give monomethyl products according to the equation,

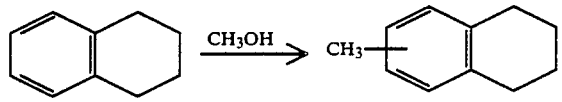

The tetralin is reacted with methanol over a bed of solid acidic catalyst. The molar proportions of tetralin and methanol have an important influence on the reaction. In particular, methanol undergoes dehydration under reaction conditions to afford dimethyl ether and water. Water deactivates the catalyst, therefore the reaction temperature needs to be increased with increasing water (and methanol) concentration. But increasing the reaction temperature undesirably leads to an increase in byproduct formation and tends to increase tetralin decomposition as reflected in a decrease in selectivity at a constant high conversion (or a decrease in conversion at a constant high selectivity). Consequently, increasing the relative amounts of methanol leads to increased tetralin decomposition because of increased methylation reaction temperature resulting from deactivation of the catalyst by water formation. On the other hand, increasing the molar proportion of methanol increases the production rate of reaction products, everything else being equal. Consequently, the amount of methanol relative to tetralin which is used in the reaction mixture is a balance of the adverse effect of increased reaction temperature and the beneficial effect of increased production rate. It has been found that a tetralin-methanol mixture containing from about 1 to about 15 weight percent of methanol relative to the methanol-tetralin mixture (24 to 1.4 molar proportions of tetralin relative to methanol) appears to afford the most favorable reaction regime. Methanol concentrations between about 1 and 8 weight percent appear especially desirable (24 to 2.8 molar proportions of tetralin) and those between about 2 and 6 weight percent (12 to 3.8 molar proportions) may be optimum. But it must be realized and recognized that increasing methanol concentration leads to an increase in reaction temperature.

Tetralin is reacted with methanol over a solid acidic catalyst. Silica-aluminas generally function satisfactorily as the solid acidic catalyst of this invention, especially amorphous, cogelled silica-aluminas as arising from the oil dropping method, with the silica-alumina ratio varying between about 60:40 up to about 95:5. Those with silica-alumina ratios between about 85:15 and 95:5 seem particularly well suited. Ammonium fluorosilicate-treated silica-aluminas also function well in the practice of the invention. These are silica-aluminas which have been dealuminated with ammonium fluorosilicate as described in U.S. Ser. No. 404,550, filed 9/7/89.

It has been observed that zeolite $\beta$ is a particularly advantageous catalyst for use in the monomethylation of tetralin, particularly because of its increased activity permitting a substantially lower reaction temperature. Zeolite $\beta$ is characterized by a high silica-alumina ratio and has been described in U.S. Pat. No. 3,308,069 and Re 28,341, both of which are incorporated by reference, as well as European Patent Applications 95304, 159846, 159847, and 164,939, which also are incorporated by reference. In our invention zeolite $\beta$ is a particularly preferred solid acid catalyst.

Suitable solid acid catalysts must have a selectivity of at least 65% under conditions where there is at least 65% conversion of tetralin, and preferably exhibit a selectivity of at least 75%, even more preferably of at least 80%. The selectivity, S, is defined by the equation $$S = \frac{W_{5/6} \times 100}{W_{tot}}$$

where $W_{5/6}$ is the combined weight of 5-methyltetralin and 6-methyltetralin and $W_{tot}$ is the weight of all reaction products.

The percent conversion is defined somewhat differently than usual. Under any reaction conditions there is a theoretical maximum amount of tetralin which could react with methanol to give exclusively monomethyltetralins. We designate this theoretical maximum amount as $A_{max}$. We designate the total amount of tetralin which is consumed under the reaction conditions as $A_{tot}$. The percent conversion, C, is defined as, $$C = \frac{A_{tot} \times 100}{A_{max}}$$

It is preferred that conversions of at least 65% be attained, and conversions of at least 80% are more desirable, with conversions of at least 90% most desirable. We emphasize again that the operative reaction regime has $S \geq 65\%$ where $C \geq 65\%$. But to avoid the adverse effects of tetralin decomposition products in the product mixture, it is required that tetralin conversion not exceed about 120%.

The reaction is preferably, although not necessarily, conducted in the liquid phase, which implies a reaction pressure of approximately 1500 psig depending upon the reaction temperature. As stated previously, the reaction temperature is a function of methanol concentration and is as well a function of the particular solid acid catalyst used, and must be experimentally determined. For example, using an approximately 2% methanol-tetralin feedstock, the appropriate reaction temperature is between about 350° and 375° C. for a 90:10 silica-alumina, but is optimally only about 250°–275° C. for zeolite β. To illustrate further using zeolite β as the solid acid catalyst, at a 2% level of methanol in the feedstock the reaction temperature is in the 250°–275° C. range whereas for 3% methanol in the feedstock the methylation temperature is in the range of 325°–350° C.

The preferred mode of operation for our invention is a continuous methylation of tetralin using a bed of the solid acid catalyst, most usually as a fixed bed. The methanol-tetralin feedstock, containing between about 1 and about 15 weight percent methanol (from about 24 to about 1.4 molar proportions of tetralin relative to methanol) is passed in the liquid phase over the bed of solid acid catalyst, which is preferably zeolite β. The feedstock may be passed either upflow or downflow, although operation downflow in the trickle bed mode is somewhat more convenient. Where a liquid phase alkylation is desired, the pressure will be maintained at a level sufficient to ensure that all reactants and products are maintained in the liquid phase. The reaction temperature will depend principally on methanol concentration in the feedstock and the solid acid catalyst. For the catalysts of this invention within the stated methanol range the reaction temperature will vary between about 200° C. and 400° C. For all the reasons stated previously, it is preferable to conduct the reaction at as low a temperature as is feasible. The flow rate of the feedstock also will depend upon methylation conditions, such as temperature and catalyst used, but at the temperatures appropriate for the use of zeolite β as the solid acid catalyst a flow rate of about 14 weight hourly space velocity is more or less typical. However, it should be recognized that this is not a particularly critical process variable and can readily be determined by the skilled worker.

The examples that follow are merely illustrative of the process that is my invention and do not limit it in any way.

EXAMPLES

General Experimental Procedure

The pilot plant used to evaluate catalysts for methylation of tetralin consisted of a feed vessel containing the methanol/tetralin feed and a feed pump for charging the feed to the reactor and a reactor section. The reactor was a vertical ⅜" ID stainless steel pipe ca. 3 ft in length fitted with a spiral pre-heater in the lower section of the pipe. The reactor was housed inside of a tube furnace. A thermocouple probe extended into the center of the reactor and allowed direct measurement of reaction temperature in the catalyst zone. The catalyst to be tested (5.6 g) was mixed with an equal volume of sand and loaded into the reactor above the pre-heater. The purpose of the sand packed catalyst bed is to provide improved liquid flow characteristics through the catalyst bed thereby reducing the likelihood of channeling and bypassing of the reactant stream. After loading, the catalyst bed depth was ca. 6". Downstream of the reactor the product was depressed and sampled for analysis. The test run was begun by the following procedure. The catalyst was treated in the reactor at 450° C. in flowing nitrogen for 1 hr then cooled to room temp. The reactant feed solution was pumped upflow at 83 g/hr through the bottom of the reactor with reactor pressure maintained at 1500 psig. Heat-up to reaction temperature then was started.

A tetralin-methanol feedstock was passed upflow over the fixed bed of catalyst in the aforedescribed reactor under varying reaction conditions and product was analyzed for at least 3 consecutive periods of 4 hours each. Product was analyzed during each period for tetralin, 5-methyltetralin, and 6-methyltetralin. From the analytical data an average selectivity and average conversion (both as defined previously) was calculated for the particular reaction conditions from data representing equilibrium conditions. Either methanol concentration or the reaction temperature then was changed, product was sampled and analyzed for at least 3 periods of 4 hours each, and the average selectively and conversion again determined under this second set of reaction conditions. Often the reactor was not lined out (i.e., not at equilibrium) for the first period following a change, and these data points were not included in determining the average selectivity and average conversion. Consequently, one long continuous run afforded data, as reproduced in the following tables, which rather completely characterized the reaction regime in terms of average selectivity and conversion as a function of reaction temperature, methanol concentration, and solid acid catalyst.

Analyses of feed and product mixtures were performed by gas chromatography using a flame ionization detector and a Restek 30 meter $RT_x-1$ column, 0.32 mm I.D.×0.1 micron film. Hydrogen was the carrier gas at 5 psig head pressure, 150 cc per minute split flow, temperature programmed from 50°–150° C. at 5°/min. and 150°–270° C. at 20°/min.

Catalyst A

Amorphous, Cogelled silica-alumina, (90:10)

This catalyst was prepared by the well known oil-dropping method. See, for example, the description in U.S. Pat. No. 4,870,222. Results are summarized in Table 1.

Catalyst B

Amorphous, Cogelled silica-alumina, 75:25

This material is analogous to that above, differing principally in the silica to alumina ratio. Results are summarized in Table 2.

Catalyst C

Dealuminated 75:25 silica-alumina

Catalyst B was treated with ammonium trifluorosilicate as described in U.S. Ser. No. 404,550, filed Sept. 7, 1989, in an amount equivalent to 14 mole percent aluminum present in Catalyst B. Results are summarized in Table 3.

Catalyst D

Zeolite Beta

A sample of this material was prepared as follows. To 361.4 g tetraethylammonium hydroxide (40 weight percent) was added 51.7 g $NaAlO_2$ (27.1 weight percent water). The mixture was heated to and maintained at reflux while being stirred for 10 minutes. The mixture, which still contained undissolved $NaAlO_2$, was transferred to a larger container and mixed vigorously with a Heidolph mixer until the temperature dropped to about 40° C. To the cold mixture was added 945 g of Ludox LS (31.3 weight percent silica) over 2 hours. The gel was transferred to a 2 liter stirred autoclave where it was heated to 150° C. during an interval of 2 hours then held at 150° C. for 144 hours. The cooled reaction mixture was centrifuged at 2,000 RPM and solid was washed with deionized water until the pH of the mother liquor was below 10. The resulting solid was dried at room temperature prior to calcination. The calcination cycle consisted of heating from 100° to 350° C. in 1 hour, maintenance at 350° C. for 1 hour, heating from 350° to 600° C. over 1 hour, and holding the mass at 600° C. for 2 hours. The calcined solid was ammonium exchanged with a 20-25% solution of aqueous ammonium chloride containing 5 times the weight of the zeolite as ammonium chloride. After the mixture was stirred for 1 hour at 95°-100° C. the mixture was filtered and solid was washed with some deionized water. This ammonium exchange was repeated twice more, and the solid from the third exchange was washed repeatedly with deionized water until the filtrate tested negative for chloride using 10% silver nitrate solution. Results are summarized in Table 4.

TABLE 1

Methylation of Tetralin with 90:10 Silica:alumina, 1.85 Weight Percent Methanol in Feed

| Period | Temperature °C. | Percent Tetralin[a] | 6-MT[b] | 5-MT[c] | Selectivity | Conversion[d,e] |
|---|---|---|---|---|---|---|
| 1 | 175 | 98.89 | 0.00 | 0.00 | 0.00 | 0.17 |
| 2 | 175 | 99.09 | 0.00 | 0.00 | 0.00 | 0.00 |
| 3 | 175 | 99.02 | 0.00 | 0.00 | 0.00 | 0.00 |
| 4 | 200 | 99.05 | 0.00 | 0.00 | 0.00 | 0.00 |
| 5 | 200 | 98.52 | 0.00 | 0.00 | 0.00 | 5.02 |
| 6 | 200 | 98.87 | 0.00 | 0.00 | 0.00 | 0.39 |
| 7 | 225 | 98.93 | 0.00 | 0.00 | 0.00 | 0.00 |
| 8 | 225 | 98.93 | 0.00 | 0.00 | 0.00 | 0.00 |
| 9 | 225 | 98.67 | 0.00 | 0.00 | 0.00 | 3.03 |
| 10 | 250 | 98.96 | 0.00 | 0.00 | 0.00 | 0.00 |
| 11 | 250 | 98.36 | 0.00 | 0.00 | 0.00 | 7.10 |
| 12 | 250 | 98.77 | 0.03 | 0.04 | 53.81 | 1.72 |
| 13 | 250 | 98.78 | 0.04 | 0.05 | 78.83 | 1.52 |
| 14 | 275 | 98.68 | 0.09 | 0.10 | 86.72 | 2.90 |
| 15 | 275 | 98.47 | 0.15 | 0.18 | 76.90 | 5.67 |
| 16 | 275 | 98.50 | 0.14 | 0.19 | 82.78 | 5.27 |
| 17 | 300 | 97.22 | 0.53 | 0.67 | 71.77 | 21.95 |
| 18 | 300 | 97.20 | 0.64 | 0.85 | 87.72 | 22.26 |
| 19 | 300 | 97.28 | 0.64 | 0.82 | 90.23 | 21.20 |
| 21 | 325 | 94.73 | 1.57 | 1.98 | 85.29 | 54.68 |
| 22 | 325 | 94.63 | 1.67 | 2.09 | 87.92 | 55.96 |
| 23 | 350 | 92.92 | 2.29 | 2.64 | 82.35 | 78.34 |
| 24 | 350 | 92.16 | 2.65 | 3.06 | 84.84 | 88.27 |
| 25 | 350 | 92.25 | 2.55 | 2.96 | 82.78 | 87.11 |
| 26 | 350 | 92.27 | 2.59 | 3.03 | 84.89 | 86.81 |
| 27 | 350 | 92.53 | 2.54 | 3.02 | 87.41 | 83.42 |
| 28 | 350 | 92.53 | 2.46 | 2.91 | 84.42 | 83.45 |
| 29 | 350 | 92.59 | 2.42 | 2.89 | 84.27 | 82.67 |
| 30 | 350 | 92.75 | 2.36 | 2.81 | 84.19 | 80.58 |
| 31 | 350 | 92.95 | 2.23 | 2.66 | 82.13 | 78.01 |
| 32 | 375 | 92.41 | 2.55 | 2.72 | 81.20 | 85.09 |
| 33 | 375 | 92.34 | 2.51 | 2.42 | 75.16 | 85.95 |
| 34 | 375 | 92.43 | 2.53 | 2.43 | 76.67 | 84.77 |
| 35 | 375 | 92.54 | 2.47 | 2.39 | 76.42 | 83.33 |
| 36 | 375 | 92.66 | 2.46 | 2.41 | 78.05 | 81.76 |
| 37 | 400 | 92.64 | 2.03 | 1.72 | 59.91 | 82.02 |
| 38 | 400 | 92.39 | 1.52 | 1.03 | 39.17 | 85.29 |
| 39 | 400 | 92.43 | 1.52 | 1.05 | 39.72 | 84.77 |

[a]Percent of all hydrocarbons in feedstock.
[b]6-Methyltetralin produced.
[c]5-Methyltetralin produced.
[d]Percent of theoretically maximum tetralin conversion.
[e]Theoretical maximum tetralin conversion is 6.90%.

TABLE 2

Methylation of Tetralin with Catalyst B 1.43 Weight Percent Methanol in Feed

| Period | Temperature °C. | Percent Tetralin[a] | 6-MT[b] | 5-MT[c] | Selectivity | Conversion[d,e] |
|---|---|---|---|---|---|---|
| 1 | 315 | 95.69 | 1.11 | 1.42 | 75.12 | 56.94 |
| 2 | 315 | 95.72 | 1.07 | 1.36 | 73.15 | 56.32 |
| 4 | 325 | 95.28 | 1.25 | 1.60 | 75.63 | 63.79 |
| 5 | 325 | 94.25 | 1.67 | 2.12 | 78.88 | 81.29 |
| 6 | 325 | 94.12 | 1.72 | 2.18 | 79.03 | 83.51 |
| 8 | 300 | 96.96 | 0.58 | 0.75 | 64.18 | 35.34 |
| 9 | 300 | 97.14 | 0.49 | 0.64 | 59.70 | 32.31 |
| 10 | 275 | 97.41 | 0.39 | 0.51 | 55.43 | 27.74 |
| 11 | 275 | 98.16 | 0.16 | 0.21 | 41.86 | 15.11 |
| 12 | 275 | 98.47 | 0.15 | 0.19 | 59.26 | 9.80 |
| 14 | 250 | 98.87 | 0.03 | 0.04 | 39.71 | 3.02 |
| 15 | 250 | 98.92 | 0.02 | 0.03 | 40.36 | 2.12 |
| 17 | 325 | 96.10 | 1.12 | 1.45 | 86.98 | 49.98 |
| 18 | 325 | 95.09 | 1.46 | 1.85 | 83.49 | 67.10 |
| 20 | 350 | 92.46 | 2.51 | 3.00 | 83.77 | 111.65 |
| 21 | 350 | 92.17 | 2.60 | 3.11 | 83.15 | 116.51 |
| 22 | 385 | 92.04 | 2.63 | 2.88 | 78.64 | 118.85 |
| 23 | 385 | 91.85 | 2.70 | 2.32 | 69.75 | 122.03 |

[a]Percent of all hydrocarbons in feedstock.
[b]6-Methyltetralin produced.
[c]5-Methyltetralin produced.
[d]Percent of theoretically maximum tetralin conversion.
[e]Theoretical maximum tetralin conversion is 6.90%.

TABLE 3

Methylation of Tetralin with Catalyst C 1.65 Weight Percent Methanol in Feed

| Period | Temperature °C. | Percent Tetralin[a] | 6-MT[b] | 5-MT[c] | Selectivity | Conversion[d,e] |
|---|---|---|---|---|---|---|
| 1 | 250 | 98.28 | 0.03 | 0.06 | 21.86 | 6.11 |
| 2 | 250 | 97.95 | 0.03 | 0.04 | 9.44 | 10.99 |
| 3 | 250 | 98.07 | 0.04 | 0.03 | 11.24 | 9.25 |
| 4 | 275 | 98.18 | 0.08 | 0.11 | 37.17 | 7.58 |
| 5 | 275 | 97.53 | 0.09 | 0.11 | 17.22 | 17.24 |
| 6 | 275 | 98.02 | 0.09 | 0.11 | 29.86 | 9.93 |
| 8 | 300 | 97.14 | 0.35 | 0.45 | 51.87 | 22.91 |
| 9 | 300 | 97.52 | 0.31 | 0.41 | 61.59 | 17.31 |
| 10 | 325 | 96.34 | 0.81 | 1.02 | 77.43 | 34.58 |
| 11 | 325 | 95.65 | 1.07 | 1.37 | 79.97 | 44.71 |
| 12 | 325 | 95.75 | 1.08 | 1.38 | 83.11 | 43.37 |
| 13 | 350 | 94.95 | 1.36 | 1.72 | 81.96 | 55.05 |
| 14 | 350 | 93.29 | 1.93 | 2.37 | 79.42 | 79.53 |
| 15 | 350 | 92.71 | 2.16 | 2.62 | 79.93 | 87.95 |
| 16 | 375 | 92.52 | 2.20 | 2.28 | 72.61 | 90.72 |
| 17 | 375 | 91.99 | 2.43 | 2.10 | 67.53 | 98.55 |
| 18 | 375 | 90.84 | 2.63 | 2.18 | 61.21 | 115.45 |
| 19 | 400 | 86.61 | 2.50 | 1.82 | 35.74 | 177.59 |
| 20 | 400 | 85.85 | 2.03 | 1.20 | 25.14 | 188.76 |
| 21 | 400 | 85.87 | 2.12 | 1.23 | 26.11 | 188.46 |
| 22 | 375 | 88.21 | 2.87 | 2.23 | 48.62 | 154.09 |
| 23 | 375 | 90.64 | 3.03 | 3.13 | 76.44 | 118.39 |
| 24 | 375 | 90.77 | 2.99 | 3.11 | 76.94 | 116.48 |
| 25 | 375 | 90.81 | 2.94 | 3.04 | 75.81 | 115.89 |
| 26 | 375 | 90.91 | 2.87 | 2.98 | 75.11 | 114.42 |
| 27 | 375 | 90.88 | 2.87 | 2.98 | 74.91 | 114.81 |
| 28 | 375 | 91.45 | 2.73 | 2.86 | 77.21 | 106.48 |
| 29 | 375 | 90.41 | 2.63 | 2.78 | 65.33 | 121.83 |
| 30 | 375 | 91.58 | 2.63 | 2.81 | 76.32 | 104.56 |
| 31 | 375 | 91.87 | 2.53 | 2.74 | 77.27 | 100.33 |
| 32 | 375 | 91.76 | 2.43 | 2.66 | 73.30 | 101.94 |
| 33 | 375 | 92.39 | 2.37 | 2.61 | 78.95 | 92.64 |
| 34 | 375 | 92.69 | 2.24 | 2.49 | 78.69 | 88.27 |
| 35 | 375 | 93.00 | 2.21 | 2.41 | 81.18 | 83.78 |
| 36 | 375 | 93.07 | 2.04 | 2.33 | 77.58 | 82.73 |
| 37 | 375 | 93.47 | 1.95 | 2.23 | 79.81 | 76.79 |

TABLE 3-continued

Methylation of Tetralin with Catalyst C
1.65 Weight Percent Methanol in Feed

| Period | Temperature °C. | Percent Tetralin[a] | 6-MT[b] | 5-MT[c] | Selectivity | Conversion[d,e] |
|---|---|---|---|---|---|---|
| 38 | 375 | 93.40 | 1.93 | 2.21 | 78.19 | 77.79 |
| 39 | 375 | 93.65 | 1.80 | 2.08 | 76.75 | 74.17 |
| 40 | 375 | 94.45 | 1.59 | 1.87 | 81.29 | 62.39 |
| 41 | 375 | 94.59 | 1.50 | 1.79 | 80.08 | 60.36 |
| 42 | 375 | 94.44 | 1.53 | 1.80 | 78.26 | 62.50 |
| 43 | 375 | 94.43 | 1.49 | 1.79 | 76.84 | 62.71 |
| 44 | 375 | 95.09 | 1.30 | 1.60 | 80.44 | 52.95 |
| 45 | 375 | 96.87 | 0.64 | 0.79 | 78.54 | 26.79 |
| 46 | 350 | 96.78 | 0.65 | 0.82 | 76.62 | 28.18 |
| 47 | 350 | 96.73 | 0.65 | 0.82 | 74.68 | 28.92 |
| 48 | 350 | 97.31 | 0.54 | 0.68 | 88.58 | 20.37 |
| 49 | 350 | 96.72 | 0.52 | 0.65 | 59.34 | 29.03 |

[a]Percent of all hydrocarbons in feedstock.
[b]6-Methyltetralin produced.
[c]5-Methyltetralin produced.
[d]Percent of theoretically maximum tetralin conversion.
[e]Theoretical maximum tetralin conversion is 6.90%.

TABLE 4

Methylation of Tetralin with Zeolite Beta

| Period | Percent Methanol | Temperature °C. | Percent Tetralin[a] | 6-MT[b] | 5-MT[c] | Selectivity | Conversion[d,e] |
|---|---|---|---|---|---|---|---|
| 1 | 1.85 | 250 | 90.97 | 2.92 | 3.72 | 83.70 | 103.96 |
| 2 | 1.85 | 250 | 90.55 | 2.92 | 3.60 | 78.17 | 109.38 |
| 3 | 1.85 | 250 | 90.88 | 3.10 | 3.76 | 85.63 | 105.10 |
| 4 | 1.85 | 275 | 90.22 | 3.85 | 3.26 | 81.92 | 113.73 |
| 5 | 1.85 | 275 | 90.00 | 4.15 | 3.21 | 82.64 | 116.65 |
| 6 | 1.85 | 275 | 89.89 | 4.20 | 3.15 | 81.52 | 118.09 |
| 8 | 1.85 | 300 | 87.02 | 4.79 | 2.18 | 58.70 | 155.71 |
| 9 | 1.85 | 300 | 87.09 | 4.83 | 2.18 | 59.33 | 154.78 |
| 11 | 1.85 | 325 | 72.56 | 4.27 | 2.02 | 23.88 | 345.16 |
| 12 | 1.85 | 325 | 73.98 | 4.28 | 2.00 | 25.20 | 326.54 |
| 13 | 1.85 | 325 | 75.94 | 4.35 | 2.02 | 27.76 | 300.83 |
| 14 | 1.85 | 325 | 75.71 | 4.36 | 2.04 | 27.60 | 303.85 |
| 15 | 1.85 | 325 | 76.69 | 4.30 | 2.01 | 28.41 | 291.01 |
| 17 | 1.85 | 250 | 91.39 | 2.29 | 3.40 | 75.82 | 98.36 |
| 18 | 1.85 | 250 | 91.56 | 2.88 | 3.37 | 85.08 | 96.18 |
| 19 | 1.85 | 250 | 91.63 | 2.83 | 3.33 | 84.73 | 95.24 |
| 20 | 1.85 | 250 | 91.41 | 2.81 | 3.32 | 81.80 | 98.18 |
| 21 | 1.85 | 250 | 91.57 | 2.86 | 3.36 | 84.79 | 96.00 |
| 22 | 1.85 | 250 | 91.58 | 2.81 | 3.31 | 83.71 | 95.89 |
| 24 | 1.85 | 225 | 96.12 | 1.01 | 1.17 | 78.11 | 36.42 |
| 25 | 1.85 | 225 | 96.03 | 1.01 | 1.18 | 76.54 | 37.55 |
| 26 | 1.85 | 225 | 96.08 | 0.94 | 1.11 | 72.70 | 36.94 |
| 28 | 1.85 | 200 | 98.41 | 0.11 | 0.12 | 47.18 | 6.43 |
| 29 | 1.85 | 200 | 98.36 | 0.10 | 0.11 | 39.05 | 7.10 |
| 30 | 1.85 | 240 | 94.42 | 1.13 | 1.35 | 55.36 | 58.70 |
| 31 | 1.85 | 240 | 94.14 | 1.83 | 2.18 | 84.11 | 62.39 |
| 32 | 1.85 | 240 | 93.91 | 1.82 | 2.14 | 79.35 | 65.38 |
| 33 | 1.85 | 240 | 94.46 | 1.73 | 2.08 | 85.67 | 58.19 |
| 34 | 1.85 | 240 | 94.14 | 1.62 | 1.95 | 75.14 | 62.33 |
| 35 | 1.85 | 240 | 94.28 | 1.73 | 2.10 | 82.76 | 60.54 |
| 36 | 1.85 | 240 | 94.17 | 1.66 | 2.03 | 78.02 | 61.97 |
| 37 | 1.85 | 240 | 94.86 | 1.59 | 1.92 | 86.74 | 52.92 |
| 38 | 1.85 | 240 | 94.81 | 1.51 | 1.82 | 81.43 | 53.59 |
| 39 | 1.85 | 240 | 94.67 | 1.51 | 1.84 | 79.20 | 55.42 |
| 40 | 1.85 | 240 | 94.73 | 1.49 | 1.82 | 79.37 | 54.67 |
| 41 | 1.85 | 240 | 94.53 | 1.47 | 1.80 | 74.65 | 57.27 |
| 42 | 1.85 | 240 | 94.92 | 1.39 | 1.72 | 78.15 | 52.14 |
| 43 | 1.85 | 240 | 94.96 | 1.34 | 1.64 | 75.64 | 51.62 |
| 44 | 1.85 | 240 | 94.87 | 1.30 | 1.60 | 71.95 | 52.85 |
| 45 | 1.85 | 240 | 95.26 | 1.25 | 1.55 | 77.10 | 47.66 |
| 46 | 1.85 | 240 | 95.43 | 1.20 | 1.49 | 77.49 | 45.40 |
| 47 | 2.59 | 240 | 95.57 | 1.13 | 1.40 | 74.53 | 31.66 |
| 48 | 2.59 | 240 | 96.25 | 0.98 | 1.20 | 80.57 | 25.29 |
| 49 | 2.59 | 240 | 95.68 | 0.80 | 0.98 | 54.39 | 30.63 |
| 50 | 2.59 | 240 | 96.20 | 0.83 | 1.03 | 67.57 | 25.76 |
| 51 | 2.59 | 240 | 96.74 | 0.85 | 1.04 | 85.26 | 20.73 |
| 52 | 2.59 | 240 | 97.00 | 0.74 | 0.90 | 84.03 | 18.30 |
| 54 | 3.19 | 240 | 95.14 | 1.12 | 1.39 | 67.41 | 28.30 |
| 55 | 3.19 | 240 | 97.35 | 0.48 | 0.56 | 68.32 | 11.54 |
| 56 | 3.19 | 240 | 96.79 | 0.48 | 0.56 | 50.15 | 15.76 |
| 57 | 3.19 | 240 | 96.48 | 0.45 | 0.52 | 40.68 | 18.13 |
| 60 | 1.85 | 240 | 96.44 | 0.89 | 1.10 | 80.80 | 32.25 |
| 61 | 1.85 | 240 | 95.76 | 1.03 | 1.31 | 74.43 | 41.12 |
| 62 | 1.85 | 240 | 96.22 | 1.06 | 1.26 | 86.81 | 35.10 |
| 63 | 1.85 | 240 | 96.44 | 0.97 | 1.22 | 89.16 | 32.20 |
| 64 | 1.85 | 240 | 95.45 | 1.02 | 1.25 | 65.66 | 45.19 |
| 67 | 2.59 | 175 | 98.88 | 0.00 | 0.00 | 0.00 | 0.66 |

TABLE 4-continued
Methylation of Tetralin with Zeolite Beta

| Period | Percent Methanol | Temperature °C. | Percent Tetralin[a] | 6-MT[b] | 5-MT[c] | Selectivity | Conversion[d,e] |
|---|---|---|---|---|---|---|---|
| 68 | 2.59 | 175 | 98.85 | 0.00 | 0.00 | 0.00 | 0.96 |
| 69 | 2.59 | 200 | 98.83 | 0.04 | 0.04 | 65.08 | 1.16 |
| 70 | 2.59 | 200 | 98.92 | 0.00 | 0.00 | 0.00 | 0.32 |
| 71 | 2.59 | 200 | 98.68 | 0.02 | 0.03 | 18.83 | 2.52 |
| 72 | 2.59 | 225 | 98.57 | 0.10 | 0.10 | 52.90 | 3.59 |
| 73 | 2.59 | 225 | 98.69 | 0.09 | 0.11 | 79.38 | 2.45 |
| 74 | 2.59 | 225 | 98.53 | 0.14 | 0.18 | 76.97 | 3.94 |
| 75 | 2.59 | 250 | 97.88 | 0.39 | 0.48 | 80.65 | 10.07 |
| 76 | 2.59 | 250 | 97.35 | 0.58 | 0.72 | 80.71 | 15.03 |
| 77 | 2.59 | 250 | 97.43 | 0.57 | 0.71 | 83.75 | 14.24 |
| 79 | 2.59 | 275 | 94.50 | 1.66 | 2.02 | 82.74 | 41.64 |
| 80 | 2.59 | 275 | 94.53 | 1.68 | 2.05 | 84.19 | 41.41 |
| 82 | 2.59 | 300 | 91.24 | 3.12 | 3.30 | 83.29 | 72.18 |
| 83 | 2.59 | 300 | 91.18 | 3.09 | 3.25 | 81.61 | 72.72 |
| 85 | 2.59 | 325 | 87.90 | 4.85 | 3.99 | 79.99 | 103.47 |
| 86 | 2.59 | 325 | 87.72 | 4.88 | 4.10 | 79.96 | 105.11 |
| 88 | 2.59 | 350 | 83.91 | 5.97 | 3.60 | 63.62 | 140.79 |
| 89 | 2.59 | 350 | 83.75 | 6.11 | 3.62 | 64.00 | 142.28 |
| 91 | 2.59 | 375 | 73.36 | 5.70 | 2.79 | 33.18 | 239.55 |
| 92 | 2.59 | 375 | 72.81 | 5.52 | 2.74 | 31.58 | 244.71 |
| 93 | 2.59 | 375 | 72.05 | 5.58 | 2.74 | 30.94 | 251.79 |
| 97 | 3.19 | 250 | 97.66 | 0.52 | 0.63 | 94.52 | 9.18 |
| 98 | 3.19 | 250 | 97.75 | 0.46 | 0.54 | 89.27 | 8.45 |
| 100 | 3.19 | 275 | 95.15 | 1.36 | 1.73 | 83.20 | 28.22 |
| 101 | 3.19 | 275 | 95.09 | 1.33 | 1.68 | 79.87 | 28.70 |
| 103 | 3.19 | 300 | 92.21 | 2.54 | 3.16 | 85.73 | 50.54 |
| 104 | 3.19 | 300 | 91.75 | 2.65 | 3.31 | 83.88 | 54.06 |
| 106 | 3.19 | 325 | 89.17 | 3.88 | 4.30 | 84.33 | 73.68 |
| 107 | 3.19 | 325 | 89.51 | 3.89 | 4.31 | 87.62 | 71.08 |
| 109 | 3.19 | 350 | 83.33 | 6.46 | 1.50 | 51.24 | 118.04 |
| 110 | 3.19 | 350 | 82.40 | 6.58 | 6.24 | 77.93 | 125.07 |
| 112 | 3.19 | 375 | 79.71 | 7.66 | 5.14 | 66.86 | 145.56 |
| 113 | 3.19 | 375 | 79.99 | 7.46 | 5.06 | 66.31 | 143.45 |
| 115 | 3.19 | 400 | 70.53 | 6.31 | 3.89 | 36.00 | 215.27 |
| 116 | 3.19 | 400 | 54.02 | 5.20 | 2.97 | 18.21 | 340.73 |
| 119 | 6.32 | 275 | 96.83 | 0.75 | 0.89 | 72.60 | 8.62 |
| 120 | 6.32 | 275 | 96.85 | 0.64 | 0.76 | 63.01 | 8.53 |
| 122 | 6.32 | 300 | 94.36 | 1.75 | 2.17 | 83.38 | 18.05 |
| 123 | 6.32 | 300 | 93.42 | 2.01 | 2.52 | 80.28 | 21.67 |
| 125 | 6.32 | 325 | 85.59 | 4.45 | 5.64 | 74.85 | 51.70 |
| 126 | 6.32 | 325 | 86.81 | 4.10 | 5.27 | 76.50 | 47.02 |
| 128 | 6.32 | 350 | 82.97 | 5.30 | 6.28 | 71.93 | 61.75 |
| 129 | 6.32 | 350 | 82.53 | 6.22 | 5.54 | 71.08 | 63.43 |
| 130 | 6.32 | 375 | 84.40 | 4.94 | 5.66 | 72.24 | 56.28 |
| 131 | 6.32 | 375 | 85.64 | 4.59 | 4.99 | 71.33 | 51.52 |
| 132 | 6.32 | 375 | 83.06 | 6.02 | 5.41 | 71.42 | 61.41 |
| 134 | 6.32 | 400 | 79.06 | 6.36 | 6.09 | 62.22 | 76.74 |
| 135 | 6.32 | 400 | 78.80 | 6.59 | 6.68 | 65.47 | 77.76 |
| 137 | 6.32 | 425 | 5.67 | 5.40 | 4.53 | 10.63 | 358.22 |
| 138 | 6.32 | 425 | 5.35 | 5.48 | 4.46 | 10.60 | 359.45 |
| 139 | 6.32 | 425 | 5.52 | 5.73 | 4.64 | 11.09 | 358.81 |
| 140 | 6.32 | 425 | 5.38 | 5.78 | 4.59 | 11.07 | 359.36 |
| 141 | 6.32 | 425 | 5.09 | 5.99 | 4.64 | 11.31 | 360.46 |
| 142 | 6.32 | 425 | 4.75 | 6.46 | 4.67 | 11.80 | 361.78 |
| 143 | 6.32 | 425 | 4.88 | 6.48 | 4.66 | 11.83 | 361.25 |
| 144 | 1.85 | 250 | 68.64 | 3.53 | 2.58 | 20.20 | 396.52 |
| 145 | 1.85 | 250 | 97.88 | 0.16 | 0.17 | 32.33 | 13.39 |
| 146 | 1.85 | 250 | 98.37 | 0.23 | 0.25 | 91.14 | 6.95 |
| 147 | 1.85 | 250 | 98.33 | 0.22 | 0.24 | 82.08 | 7.42 |
| 148 | 1.85 | 250 | 98.46 | 0.19 | 0.20 | 88.88 | 5.80 |
| 149 | 1.85 | 250 | 98.40 | 0.15 | 0.16 | 63.01 | 6.52 |
| 150 | 1.85 | 250 | 98.64 | 0.14 | 0.13 | 104.56 | 3.41 |
| 151 | 1.85 | 250 | 98.69 | 0.09 | 0.09 | 86.26 | 2.76 |
| 152 | 1.85 | 250 | 98.61 | 0.06 | 0.07 | 45.17 | 3.80 |
| 153 | 1.85 | 250 | 98.86 | 0.05 | 0.06 | 249.12 | 0.58 |
| 154 | 1.85 | 250 | 98.87 | 0.05 | 0.06 | 407.17 | 0.36 |
| 155 | 1.85 | 250 | 98.63 | 0.04 | 0.04 | 29.31 | 3.59 |
| 156 | 1.85 | 250 | 98.85 | 0.03 | 0.03 | 127.02 | 0.62 |
| 157 | 1.85 | 250 | 98.78 | 0.00 | 0.00 | 0.00 | 1.53 |
| 158 | 1.85 | 250 | 98.95 | 0.00 | 0.00 | 0.00 | 0.00 |
| 159 | 1.85 | 250 | 98.93 | 0.00 | 0.00 | 0.00 | 0.00 |
| 160 | 1.85 | 250 | 99.08 | 0.00 | 0.00 | 0.00 | 0.00 |

[a] Percent of all hydrocarbons in feedstock.
[b] 6-Methyltetralin produced.
[c] 5-Methyltetralin produced.
[d] Percent of theoretically maximum tetralin conversion.
[e] Theoretical maximum tetralin conversion is 6.90%.

Figure 2:
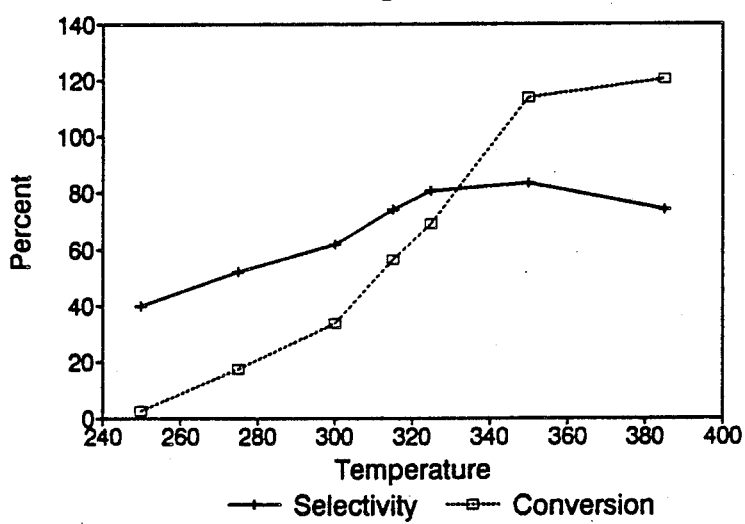
Figure 3:
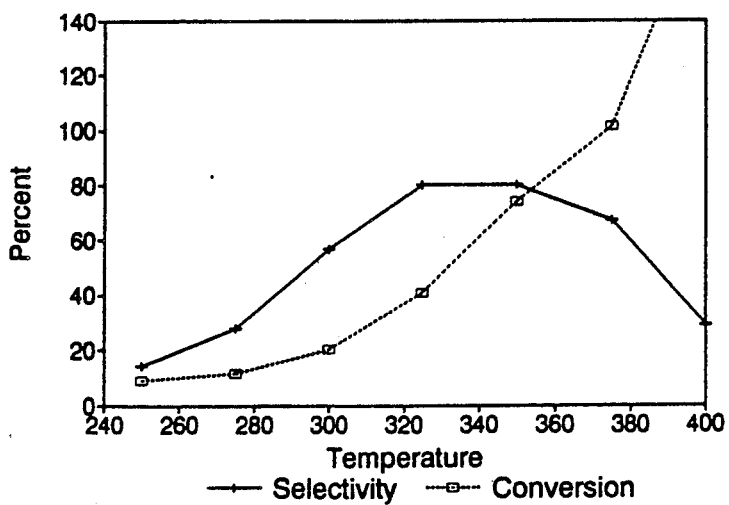
Figure 4:
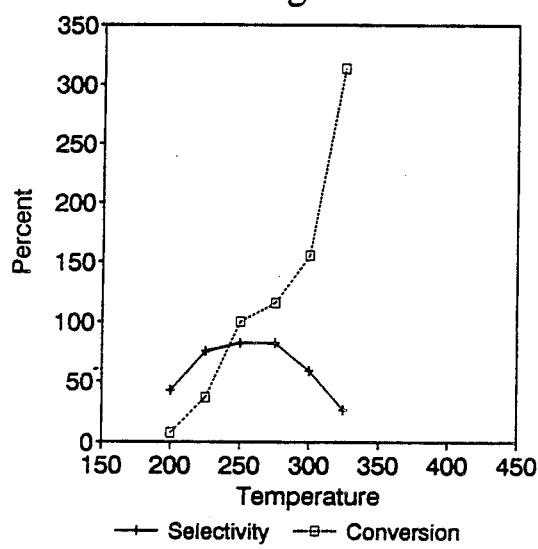
Figure 5:
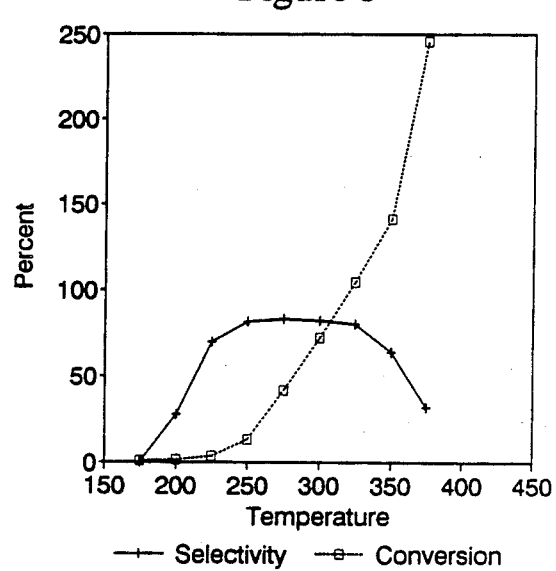
Figure 6:
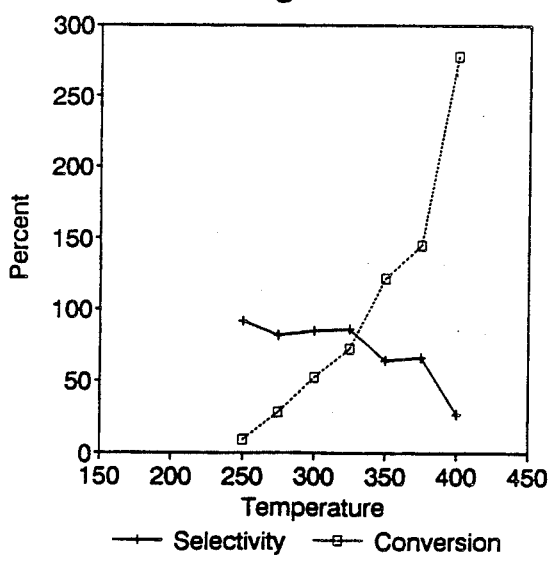
Figure 7:
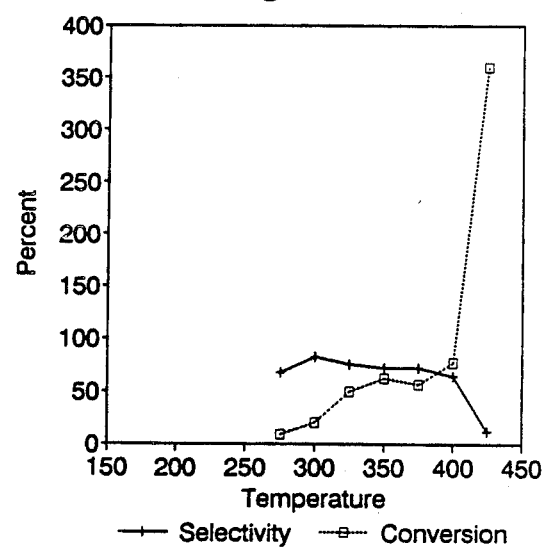

The relevant portion of the foregoing raw data is presented in Table 5, which summarizes the average selectivity and average conversion observed with various catalysts over the temperature range tested. These results are graphically portrayed in FIGS. 1–7. As the data clearly show, zeolite beta shows selectivity-conversion characteristics analogous to, e.g., catalysts A and C at 100° C. lower temperature. The data also clearly show the sensitivity of methylation to methanol concentration; whereas the temperature interval using zeolite β within which selectivity is at least 65% with a conversion of 65–120% is 250°–275° for 1.85% methanol, it is 325°–350° C. for 3.2% methanol and in the 350°–400° C. range for 6.3% methanol.

TABLE 5

| | Summary of Average Selectivity and Conversion Temperature, °C. | | | | | | | | | | |
|---|---|---|---|---|---|---|---|---|---|---|---|
| | 175 | 200 | 225 | 250 | 275 | 300 | 325 | 350 | 375 | 400 | 425 |
| CATALYST A 1.85% MeOH | | | | | | | | | | | |
| Selectivity | 0 | 0 | 0 | 33.2 | 82.1 | 83.2 | 86.6 | 84.1 | 77.5 | 46.3 | |
| Conversion | <0.1 | 1.8 | 1.0 | 2.6 | 4.6 | 21.8 | 55.3 | 83.2 | 84.2 | 84.0 | |
| CATALYST B 1.43% MeOH | | | | | | | | | | | |
| Selectivity | | | | 40.0 | 52.2 | 61.9 | 74.1 | 80.8 | 83.5 | 74.2 | |
| Conversion | | | | 2.6 | 17.6 | 33.8 | 56.6 | 69.1 | 114.1 | 120.4 | |
| CATALYST C 1.65 MeOH | | | | | | | | | | | |
| Selectivity | | | | 14.2 | 28.1 | 56.7 | 80.2 | 80.4 | 67.1 | 29.0 | |
| Conversion | | | | 8.8 | 11.6 | 20.1 | 40.9 | 74.2 | 101.6 | 185.0 | |
| CATALYST D 1.85% MeOH | | | | | | | | | | | |
| Selectivity | | 43.1 | 75.8 | 82.6 | 82.0 | 59.0 | 26.6 | | | | |
| Conversion | | 6.8 | 37.0 | 99.8 | 116.2 | 155.2 | 313.5 | | | | |
| 2.6% MeOH | | | | | | | | | | | |
| Selectivity | 13.46 | 28.0 | 69.8 | 81.7 | 83.5 | 82.5 | 80.0 | 63.8 | 31.9 | | |
| Conversion | 0.8 | 1.3 | 3.3 | 13.1 | 41.5 | 72.5 | 104.3 | 141.5 | 245.4 | | |
| 3.2% MeOH | | | | | | | | | | | |
| Selectivity | | | | 91.9 | 81.5 | 84.8 | 86.0 | 64.6 | 66.6 | 27.1 | |
| Conversion | | | | 8.8 | 28.5 | 52.3 | 72.4 | 121.6 | 144.5 | 278.0 | |
| 6.3% MeOH | | | | | | | | | | | |
| Selectivity | | | | | 67.8 | 81.8 | 75.7 | 71.5 | 71.7 | 63.9 | 11.2 |
| Conversion | | | | | 8.6 | 19.9 | 49.4 | 62.6 | 56.4 | 77.3 | 359.9 |

What is claimed is:

1. A method of preparing a mixture of 5-methyltetralin and 6-methyltetralin by the alkylation of tetralin with methanol with at least 65% conversion and no more than about 120% conversion of tetralin and at least 65% selectivity to 5-methyltetralin and 6-methyltetralin formation, comprising methylating tetralin with methanol in a tetralin-methanol feedstock containing from about 24 to about 1.4 molar proportions of tetralin per mole of methanol in the presence of zeolite β at alkylation conditions.

2. The method of claim 1 where alkylation conditions include a pressure sufficient to maintain methanol in a liquid phase.

3. The method of claim 1 where conversion is at least 80%.

4. The method of claim 3 where conversion is at least 90%.

5. The method of claim 1 where the selectivity is at least 75%.

6. The method of claim 5 where the selectivity is at least 80%.

7. The method of claim 1 where conversion is at least 80% and the selectivity is at least 75%.

8. The method of claim 1 where the feedstock contains from about 24 to about 2.8 molar proportions of tetralin per mole of methanol.

9. The method of claim 8 where the feedstock contains from about 12 to about 3.8 molar proportions of tetralin per mole of methanol.

* * * * *